(12) United States Patent
Esbeck

(10) Patent No.: US 6,957,152 B1
(45) Date of Patent: Oct. 18, 2005

(54) SYSTEM AND COMPUTER-BASED METHOD FOR TRACKING AN IMPLANTABLE MEDICAL DEVICE CHARACTERISTIC DURING A COATING PROCESS

(75) Inventor: Thomas David Esbeck, Murrieta, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 211 days.

(21) Appl. No.: 10/334,018

(22) Filed: Dec. 30, 2002

(51) Int. Cl.⁷ .......................... G06F 19/00; G01N 37/00
(52) U.S. Cl. ............................................ 702/31; 702/84
(58) Field of Search .............................. 702/22, 23, 25, 702/30–32, 81, 82, 84, 127, 170, 173; 427/2.25; 623/1.15, 1.42; 177/25.19; 700/115, 305

(56) References Cited

U.S. PATENT DOCUMENTS

| | | | | |
|---|---|---|---|---|
| 5,437,083 A | * | 8/1995 | Williams et al. ............. | 29/235 |
| 6,383,215 B1 | * | 5/2002 | Sass ........................... | 623/1.15 |
| 6,385,593 B2 | * | 5/2002 | Linberg ....................... | 705/28 |
| 6,723,373 B1 | * | 4/2004 | Narayanan et al. .......... | 427/2.25 |
| 2002/0188346 A1 | * | 12/2002 | Healy et al. ................ | 623/1.15 |
| 2003/0087024 A1 | * | 5/2003 | Flanagan .................... | 427/2.24 |
| 2004/0072922 A1 | * | 4/2004 | Hossainy et al. ........... | 523/113 |
| 2004/0073294 A1 | * | 4/2004 | Diaz et al. .................. | 623/1.42 |

* cited by examiner

Primary Examiner—Marc S. Hoff
Assistant Examiner—Manuel L. Barbee
(74) Attorney, Agent, or Firm—Squire, Sanders & Dempsey L.L.P.

(57) ABSTRACT

A system, method and computer product track a stent characteristic during a coating process. For example, a method comprises receiving an implantable medical device from a coating apparatus, after the coating apparatus has applied a coating to the implantable medical device; measuring a characteristic of the implantable medical device with the coating; determining if the characteristic of the implantable medical device with the coating is within selected parameters; and generating feedback to the coating apparatus based on the determining, the feedback informing the coating apparatus to adjust a variable for future coatings, if so determined.

53 Claims, 3 Drawing Sheets

SYSTEM AND COMPUTER-BASED METHOD FOR TRACKING AN IMPLANTABLE MEDICAL DEVICE CHARACTERISTIC DURING A COATING PROCESS

TECHNICAL FIELD

This invention relates generally to implantable medical devices, such as stents, and more particularly, but not exclusively, provides a system and method for tracking an implantable medical device characteristic during a coating process.

BACKGROUND

Blood vessel occlusions are commonly treated by mechanically enhancing blood flow in the affected vessels, such as by employing a stent. Stents act as scaffolding, functioning to physically hold open and, if desired, to expand the walls of affected vessels. Typically stents are capable of being compressed, so that they can be inserted through small lumens via catheters, and then expanded to a larger diameter once at the desired locations. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

Stents are used not only for mechanical intervention but also as vehicles for providing biological therapy. Biological therapy can be achieved by medicating the stents. Medicated stents provide for local administration of therapeutic substances at diseased sites. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition (also referred to as a coating substance) including a solvent, a polymer dissolved in the solvent, and a therapeutic substance dispersed in the blend is applied to the stent by spraying the composition onto the stent. The solvent is allowed to evaporate, leaving on the stent surfaces a coating of the polymer and the therapeutic substance impregnated in the polymer.

The process of medicating a stent generally comprises repeatedly coating the stent with various layers of composition. For quality assurance purposes, after each coating application, the stent is weighed to determine if the amount of composition applied is within parameters. If too much composition was applied, then the stent can be discarded. If too little composition was applied, then another layer can be applied.

Conventionally, the step of weighing is accomplished by placing the stent onto a balance and manually entering the weight into a spreadsheet program. The spreadsheet program can then calculate the difference between two consecutive weight measurements made before and after a layer application to calculate the weight of the layer. Based on this calculation, an operator can choose to discard the stent, reapply the coating layer, or continue the process, such as applying other coating layers. However, because it requires manual data entry after each application of a coating layer, this method is time consuming and prone to data input errors. Additionally, each time the operator handles the stent, a risk of causing damage to the coating exists.

Accordingly, a new system and method is needed that substantially reduces data input errors and the time associated with the fabrication process as well as risks associated with the operator handling of the stent.

SUMMARY

The present invention provides a system for tracking a characteristic of an implantable medical device, e.g., a stent, during a coating process. The system comprises an implantable medical device characteristic reader capable of measuring an implantable medical device characteristic; a processor, communicatively coupled to the implantable medical device characteristic reader, capable of determining if the characteristic is within preset parameters; and a feedback engine, communicatively coupled to the processor, capable of generating feedback based on the determining. In an embodiment of the invention, the measurement includes weight and the characteristic includes an applied coating layer weight. In an embodiment of the invention, the implantable medical device characteristic reader and processor are further capable of storing the measurements and/or the characteristics, respectively.

The present invention further provides a computer-based method for tracking an implantable medical device characteristic during a coating process. In one embodiment, the method comprises: measuring an implantable medical device characteristic; determining if the characteristic is within preset or selected parameters; and generating feedback based on the determining. In an embodiment of the method, the measurement includes weight and the characteristic includes an applied coating layer weight. In an embodiment of the invention, the method can further comprise storing the measurements and/or the characteristics.

Therefore, the system and method advantageously enable the tracking of implantable medical device characteristics during a coating process.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION

The following description is provided to enable any person having ordinary skill in the art to make and use the invention, and is provided in the context of a particular application and its requirements. Various modifications to the embodiments will be readily apparent to those skilled in the art, and the principles defined herein may be applied to other embodiments and applications without departing from the spirit and scope of the invention. Thus, the present invention is not intended to be limited to the embodiments shown, but is to be accorded the widest scope consistent with the principles, features and teachings disclosed herein.

Figure 1:
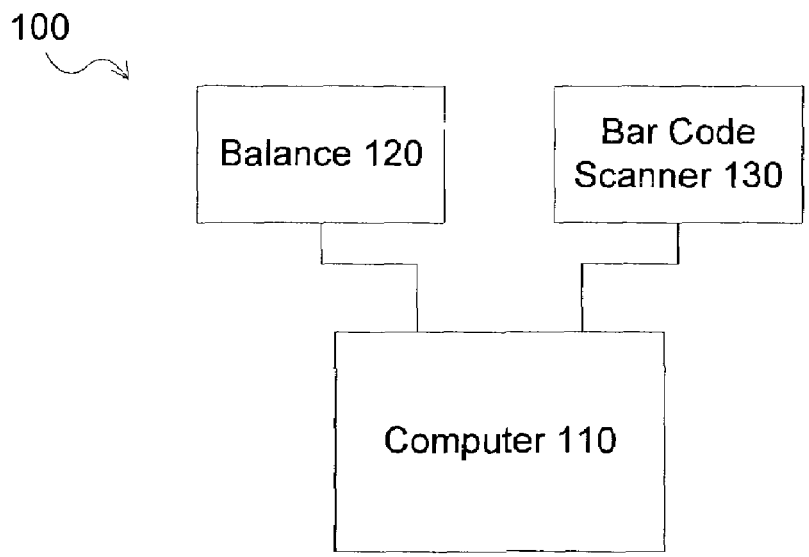
FIG. 1 is a block diagram illustrating a system in accordance with a first embodiment of the present invention.

FIG. 1 is a block diagram illustrating a system 100 in accordance with a first embodiment of the present invention. The system 100 comprises a computer 110; an implantable medical device characteristic reader, e.g., a balance 120; and an implantable medical device identifier, e.g., a bar code scanner 130. The balance 120 and bar code scanner 130 are both communicatively coupled to the computer 110. The computer 110 can include a desktop computer; laptop computer; personal digital assistant; or any other device capable of receiving and processing data from the balance 120 and bar code scanner 130. In an embodiment of the invention, the computer 110 is also communicatively coupled to a coating/sprayer apparatus and is capable of receiving apparatus identification data, spray parameters, and/or other data from the apparatus. Further, in an embodiment of the invention, the computer 110 is capable of transmitting data to the coating/sprayer system so that the system can adjust its settings. Examples of setting that can be adjusted included, but are not limited to, amount of composition being applied to the stent, flow rate of the composition, temperature of the composition, ratio of the ingredients in the composition, such as for example, the ratio of the drug to the polymer, as well as other coating conditions. The computer 110 will be discussed in further detail in conjunction with FIG. 2 below.

The balance 120 weighs stents and transmits weight data to the computer 110. In one embodiment of the invention, the balance 120 includes a Mettler Toledo Analytical Balance. In one embodiment, the balance 120 can be operably connected to the mandrel supporting the stent so as to give the operator the option of conducting the measurement without the need of removing the stent from the mandrel. Although the system is being described as including a balance 120, one skilled in the art will recognize that any implantable medical device characteristic reader can be used to measure any characteristic at issue. For example, instead of the balance 120, a spectrum analyzer can be used to measure the chemical composition or thickness of the stent and/or of the coating layer(s). Although the system is being applied to stents, one skilled in the art will recognize that the system can be applied to any implantable medical device, such as leads, valves, graft, etc.

The bar code scanner 130 scans a bar code located on a stent mandrel that supports the stent, which is weighed by the balance 120, during a coating application process. The mandrel that supports stent, can be, in one embodiment, in rotational attachment with a motor to rotate the stent about the longitudinal axis of the stent or move stent in a linear direction, back and forth, passed a spray nozzle. Linear and/or rotational movement of the stent during the spray process can lead to a more uniform coating layer. In addition, the bar code scanner 130 transmits scanned bar code information to the computer 110. Although the system is being described as including a bar code scanner 130, one skilled in the art will recognize that any implantable medical device identifier can be used to identify each implantable medical device, for example a microchip integrated with the implantable medical device. It will be appreciated that the implantable medical device identification information (e.g., the bar code) may be included on the implantable medical device or associated items, e.g., the stent mandrel, the stent itself, and/or on stent packaging.

Figure 2:
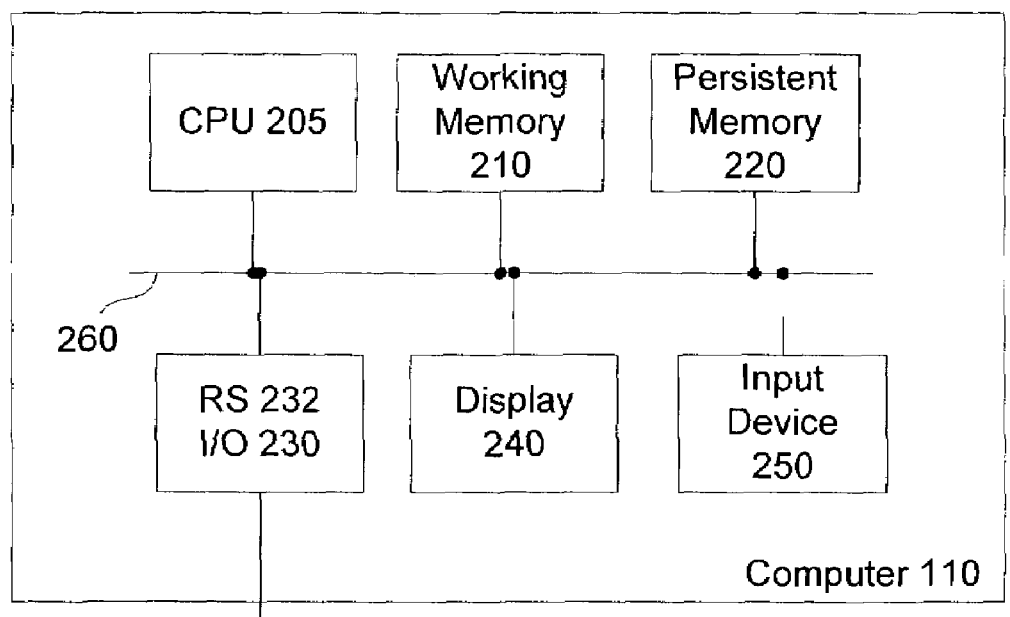
FIG. 2 is a block diagram illustrating a computer of the system of FIG. 1.

FIG. 2 is a block diagram illustrating the computer 110 of the system 100 (FIG. 1). The computer 110 includes a central processing unit (CPU) 205; working memory 210; persistent memory 220; RS232 input/output (I/O) interface 230; display 240 and input device 250, all communicatively coupled to each other via system bus 260. The CPU 205 may include an Intel Pentium® microprocessor, a Motorola PowerPC® microprocessor, or any other processor capable to execute software stored in persistent memory 220. The working memory 210 may include random access memory (RAM) or any other type of read/write memory devices or combination of memory devices. The persistent memory 220 may include a hard drive, read only memory (ROM) or any other type of memory device or combination of memory devices that can retain data after the computer 110 is shut off.

The I/O interface 230 is communicatively coupled, via wired and/or wireless techniques, to the balance 120 and scanner 130. In an alternative embodiment of the invention, the I/O 230 interface may also be communicatively coupled to other devices, such as a N1537 spray device and/or a spectrum analyzer. It will be appreciated by one of ordinary skill in the art that the I/O 230 interface may include other types of I/O 230 interfaces besides RS232-compliant interfaces. For example, the I/O 230 can include a Bluetooth-compliant I/O interface in place of an RS232-compliant interface. The display 240 may include a cathode ray tube display, flat panel display or other display device. The input device 250 may include a keyboard, mouse, or other device for inputting data, or a combination of devices for inputting data.

One skilled in the art will recognize that the computer 110 may also include additional devices, such as network connections, additional memory, additional processors, LANs, input/output lines for transferring information across a hardware channel, the Internet or an intranet, etc. One skilled in the art will also recognize that the programs and data may be received by and stored in the system in alternative ways.

Figure 3:
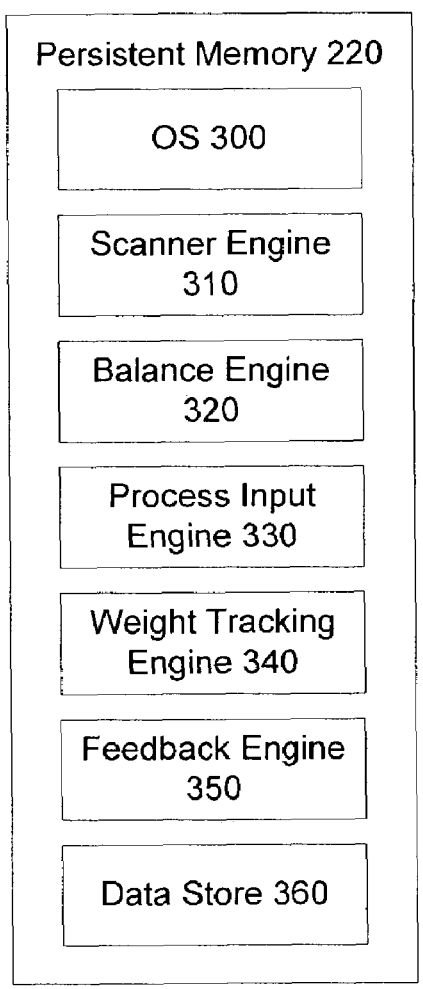
FIG. 3 is a block diagram illustrating a persistent memory of the computer for FIG. 2.

FIG. 3 is a block diagram illustrating the persistent memory 220 of the computer 110 (FIG. 2). The persistent memory 220 includes an operating system (OS) 300; a scanner engine 310 (generally, the implantable medical device characteristic reader engine); a balance engine 320 (generally, the implantable medical device identifier engine); a process input engine 330; a weight tracking engine 340 (generally, the implantable medical device characteristic tracking engine); a feedback engine 350; and a data store 360. In one embodiment of the invention, the OS 300 includes Windows 2000. However, it will be appreciated that the OS 300 can include other operating systems, such as Linux.

The scanner engine 310 communicates with the bar code scanner 130 and receives, from the scanner 130, bar code data that is associated with a stent. As mentioned above, the bar code to be scanned by the scanner 130 can be located on a stent mandrel that supports a stent during spray coating. In an alternative embodiment of the invention, the scanner engine 310 can communicate with any other type of device that can read stent-identifying information.

The balance engine 320 communicates with the balance 120 and receives stent weight data from the balance 120. In addition, the balance engine 320 stores received weight data in the data store 360 in a manner that associates the weight data with the bar code data (or other stent-identifying information). In another embodiment of the invention, instead of the balance engine 320, a different implantable medical device characteristic reader engine communicates with the implantable medical device characteristic reader that measures a different stent characteristic. For example, a spectrum analysis engine can communicate with a spectrum analyzer, receive spectrum data from the analyzer and then store this received spectrum data in the data store 360.

The process input engine 330 receives process data and stores the process data in the data store 360. Process data can include the coating substance(s) to be applied to the stent; the number of layers of the coating substance(s) to be applied to the stent; the amount of coating substance(s) to be applied to the stent; the bake time and temperature to dry the stent after the coating substance application, etc. The process data can be manually input by an operator, pre-stored on the computer 110 in the persistent memory 220, received via a network connection, and/or entered via other techniques.

The coating substance of the process can include a solvent and a polymer dissolved in the solvent and optionally a therapeutic substance or a drug added thereto. Representative examples of polymers that can be used to coat a stent include ethylene vinyl alcohol copolymer (commonly known by the generic name EVOH or by the trade name EVAL); poly(hydroxyvalerate); poly(L-lactic acid); polycaprolactone; poly(lactide-co-glycolide); poly(glycerol-sebacate); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrilestyrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Examples of solvents include, but are not limited to, dimethylsulfoxide, chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and mixtures and combinations thereof.

The therapeutic substance or drug can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, dexamethasone, and rapamycin.

The weight tracking engine 340 tracks coating layer weights by calculating the difference in weights between successive stent weight measurements (as stored in the data store 360). In addition, the weight tracking engine 340 compares the calculated coating layer weights to weights specified in stored process data in the data store 360. Although a weight tracking engine 340 is described, one skilled in the art will recognize that any implantable medical device characteristic tracking engine can be used.

The feedback engine 350, based on the comparison made by the weight tracking engine 340, then provides visual, audio, and/or other types of feedback (e.g., tactile) to an operator. The feedback can include instructions to reapply the coating substance to the stent due to a low weight, instructions to discard the stent due to excessive coating, or instructions to continue the coating process since the measured weight (or other characteristic) is within process parameters as indicated in the process data in the data store 360. In an embodiment of the invention, the feedback engine 350 can also provide feedback to a sprayer apparatus coupled to the computer 110. For example, the feedback engine 350 could instruct the sprayer apparatus to increase or decrease the amount of coating substance applied to the stent based on the comparison made by the weight tracking engine 340. Other instruction could include, for example, adjusting the temperature of the spray nozzle head, adjusting the ratio of the ingredients of the coating substance (e.g., the ratio between the polymer and the solvent or the ratio between the polymer and the drug), adjusting the atomization pressure of the nozzle, adjusting the flow rate of the composition, etc.

In another embodiment of the invention, the feedback engine 350 can transmit feedback to other people, such as process engineers, via a network connection. This feedback might indicate process problems, such as consistently too much or too little composition being applied to stents. The process engineers, using this feedback, can then modify the process and associated equipment accordingly to correct the process problems.

Figure 4:
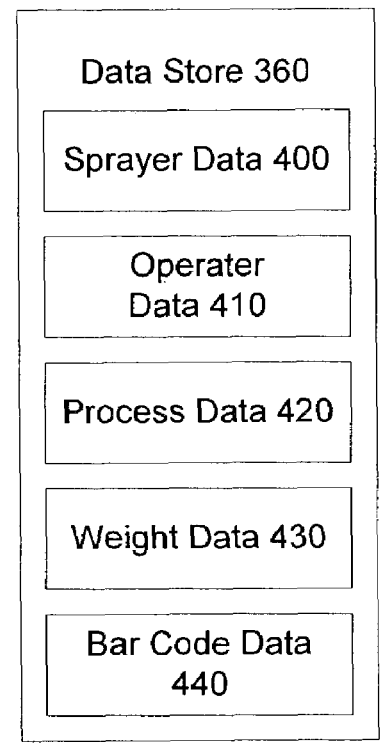
FIG. 4 is a block diagram illustrating a data store of the persistent memory of FIG. 3.

FIG. 4 is a block diagram illustrating the data store 360 of the persistent memory 220 (FIG. 3). The data store 360 includes, for each stent, sprayer data 400, operator data 410, process data 420, weight data 430 (generally, implantable medical device characteristic data) and bar code data 440 (generally, implantable medical device identification information) and is compliant with FDA section 11 regulations regarding electronic storing of records relating to medical devices. The data store 360 can be in the form of any data structure, such as a table, linked list, etc. The sprayer data 400 includes sprayer identification data as entered by an operator. In alternative embodiment of the invention, the computer 110 can interface directly with the sprayer and receive sprayer identification data from the sprayer for storing in the sprayer data 400. Further, the sprayer data 400 may also include sprayer parameters, such as atomization pressure and composition dispersion rate.

The operator data 410 includes data that identifies an operator performing the stent coating process. The data can include an employee number, name, and/or other identification data. The data can be input by the operator during a log in process or via other techniques.

The process data 420 includes parameters used in the process of coating a stent with a composition. The parameters can include composition components, amount of composition to spray per each layer application, bake time, and other factors. The process data 420 can be entered manually by an operator, can be pre-stored in the data store 360, can be received over a network, or otherwise entered in the data store 360 via other techniques.

The weight data 430 includes the weight of the stent after each layer application and/or the weight of each layer applied to the stent as calculated by the weight tracking engine 340. In another embodiment, the data 430 can include other stent characteristic data, such as the chemical composition of the coating layer as determined by a spectrum analysis of the stent.

The bar code data 440 includes bar code information that identifies a stent that is undergoing a coating process or has completed a coating process. The bar code information can be located on a stent mandrel and/or stent packaging and is stored in the bar code data 440 by the scanner engine 310. In an alternative embodiment, the bar code data 440 can include other stent identification data that is located on the stent itself, on the stent mandrel, and/or on the stent packaging.

Figure 5:
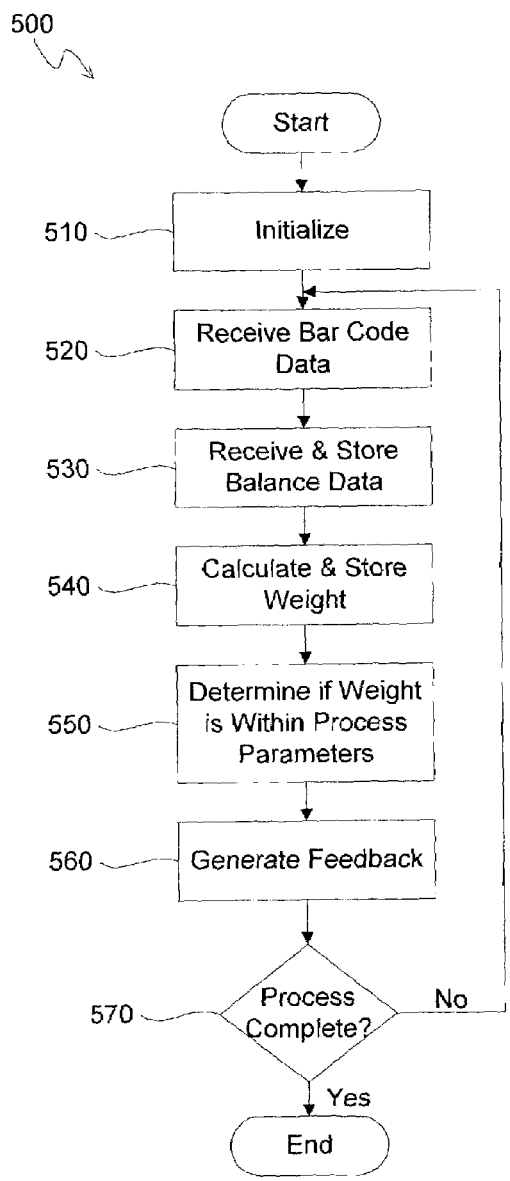
FIG. 5 is a flowchart illustrating a method of tracking a characteristic of a stent.

FIG. 5 is a flowchart illustrating a method 500 of tracking a characteristic of a stent. In an embodiment of the invention, the engines 310–340 in the persistent memory 220 can execute the method 500. First, initialization (510) occurs, as will be discussed in further detail in conjunction with FIG. 6. After initialization (510) is complete, bar code data (and/or other stent identification data) is received 520. Next, weight data of a stent that is identified by the received (520) bar code data, is received (530) from the balance 120. In addition, the received weight data can be stored (530) in the data store 360. In an alternative embodiment, other or additional data relating to a stent or coating characteristic can be received (530) and stored (530).

After the receiving (530), weight of a coating layer is calculated (540) and stored (540) in the data store 360. The weight of the coating layer is determined by comparing the weight of the stent between successive coating layer applications. If this is a first coating layer application, then the weight of the bare stent is compared with the weight of the stent after the first coating layer application. In an alternative embodiment of the invention, other stent characteristics can be calculated (540) and stored (540). For example, the chemical composition of the stent and its coatings can be calculated (540) and stored (540) using spectrum analysis.

After the calculating (540), it is determined (550) if the weight (and/or other characteristics) are within process parameters by comparing the calculated (540) characteristic (e.g., weight) with the process parameters stored in the process data 420. After the determining (550), feedback is generated (560) based on the determining. The feedback can be presented to an operator indicating the calculated characteristic exceeds parameters indicated in the process data 420 and therefore the stent should be scrapped. In addition, the feedback can indicate that the calculated characteristic is below parameters indicated in the process data 420 and therefore the coating layer needs to be reapplied. Further, the feedback can indicate that the calculated characteristic is within parameters indicated in the process data 420 and accordingly the process can continue. The feedback can be in audio, visual, and/or other formats. In addition, the feedback can be transmitted via wired or wireless techniques to other computers. In another embodiment, the feedback can be transmitted to a spray/coater apparatus so that the spray/coater apparatus can adjust its settings to meet process parameters.

After the generating (560), it is determined (570) if the process is complete (e.g., no more coating layers are to be applied to the stent). If the process is not yet complete, then the receiving (520) bar code data through the determining (570) if the process is complete are repeated. If the process is complete, then the method 500 ends.

Figure 6:
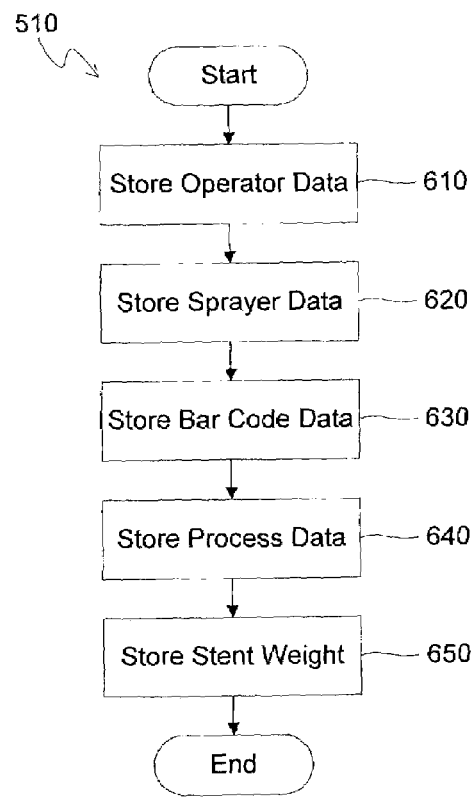
FIG. 6 is a flowchart illustrating an initialization routine of the method of FIG. 5.

FIG. 6 is a flowchart illustrating the initialization routine 510 of the method 500 (FIG. 5). The initialization routine comprises storing (610) operator data in the data store 360; storing (620) sprayer data in the data store 360; storing (630) bar code data in the data store 360; storing (640) process data in the data store 360; and storing (650) stent weight (or other characteristic) data in the data store 360. The storing (610) operator data includes storing operator identification data, such as an operator employee number, operator name, and/or other operator identification data. The storing (620) sprayer data includes storing sprayer identification data (such as sprayer type). The storing (620) can also include storing sprayer parameter data.

The storing (630) bar code data include storing stent identification data such as bar code data associated with a stent. The storing (640) process data includes storing the process parameters for a coating process for a particular stent as identified by the stored (630) bar code. Parameters can include the number of coating applications, the types of coating, bakes times, etc. The storing (650) stent weight includes storing the weight (or other characteristic) of the bare stent. All of the data for storing (610–650) can be entered manually by an operator, can be pre-stored, and/or can be received via a network connection.

The foregoing description of the illustrated embodiments of the present invention is by way of example only, and other variations and modifications of the above-described embodiments and methods are possible in light of the foregoing teaching. For example, other characteristics beside stent weight can be examined. Further, components of this invention may be implemented using a programmed general purpose digital computer, using application specific integrated circuits, or using a network of interconnected conventional components and circuits. Connections may be wired, wireless, modem, etc. The embodiments described herein are not intended to be exhaustive or limiting. The present invention is limited only by the following claims.

What is claimed is:

1. A computer-based method, comprising:
    measuring a characteristic of an implantable medical device after a coating apparatus has applied a coating to the implantable medical device;
    determining if the characteristic of the implantable medical device with the coating is within selected parameters; and
    generating feedback to the coating apparatus based on the determining, the feedback informing the coating apparatus to adjust a variable for future coatings, if so determined.

2. The method of claim 1, wherein the measuring includes weighing the implantable medical device.

3. The method of claim 1, wherein the characteristic is selected from a group consisting of coating layer weight, coating layer thickness, and composition of a coating layer.

4. The method of claim 1, further comprising presenting the generated feedback to an operator.

5. The method of claim 1, further comprising storing measurements in a data store.

6. The method of claim 1, further comprising:
    receiving implantable medical device identification data; and
    storing the identification data in a data store.

7. The method of claim 6, wherein the identification data includes bar code data.

8. The method of claim 1, further comprising storing the characteristic in a data store.

9. The method of claim 8, further comprising:
    receiving implantable medical device identification data; and
    storing the identification data in the data store.

10. The method of claim 9, wherein the identification data includes bar code data.

11. The method of claim 1, wherein the implantable medical device is a stent.

12. A system, comprising:
    means for measuring a characteristic of an implantable medical device after a coating apparatus has applied a coating to the implantable medical device;
    means for determining if the characteristic of the implantable medical device with the coating is within preset parameters; and
    means for generating feedback to the coating apparatus based on the determining, the feedback informing the coating apparatus to adjust a variable for future coatings, if so determined.

13. A computer-readable medium having stored thereon instructions to cause a processor to execute a method, the method comprising:
    measuring a characteristic of an implantable medical device after a coating apparatus has applied a coating to the implantable medical device;
    determining if the characteristic of the implantable medical device with the coating is within preset parameters; and
    generating feedback to the coating apparatus based on the determining, the feedback informing the coating apparatus to adjust a variable for future coatings, if so determined.

14. The computer-readable medium of claim 13, wherein the step of measuring includes weighing the implantable medical device.

15. The computer-readable medium of claim 13, wherein the characteristic includes coating layer weight, coating layer thickness or the composition of a coating layer disposed on the medical device.

16. The computer-readable medium of claim 13, wherein the method further comprises presenting the generated feedback to an operator.

17. The computer-readable medium of claim 13, wherein the method further comprises storing measurements in a data store.

18. The computer-readable medium of claim 13, wherein the method further comprises:
    receiving implantable medical device identification data; and
    storing the identification data in a data store.

19. The computer-readable medium of claim 18, wherein the identification data includes bar code data.

20. The computer-readable medium of claim 13, wherein the method further comprises storing the characteristic in a data store.

21. The computer-readable medium of claim 20, wherein the method further comprises:
    receiving implantable medical device identification data; and
    storing the identification data in the data store.

22. The computer-readable medium of claim 21, wherein the identification data includes bar code data.

23. The computer-readable medium of claim 13, wherein the implantable medical device is a stent.

24. A system, comprising:
    an implantable medical device characteristic reader capable of measuring a characteristic of an implantable medical device after a coating apparatus has applied a coating to the implantable medical device;
    a processor, communicatively coupled to the implantable medical device characteristic reader, capable of determining if the characteristic of the
    implantable medical device with the coating is within a selected parameter range; and
    a feedback engine, communicatively coupled to the processor, capable of generating feedback based on the determining, the feedback informing the coating apparatus to adjust a variable in future coatings, if so determined.

25. The system of claim 24, wherein the characteristic includes coating layer weight, coating layer thickness or composition of a coating layer disposed on the implantable medical device.

26. The system of claim 24, wherein the feedback engine is further capable of presenting the generated feedback to an operator.

27. The system of claim 24, wherein the implantable medical device characteristic reader is further capable of storing measurements in a data store.

28. The system of claim 24, further comprising an implantable medical device identifier capable of:
   receiving implantable medical device identification data; and
   storing the identification data in a data store.

29. The system of claim 28, wherein the identification data includes bar code data.

30. The system of claim 24, wherein the processor is further capable of storing the characteristic in a data store.

31. The system of claim 30, further comprising an implantable medical device identifier capable of:
   receiving implantable medical device identification data; and
   storing the identification data in the data store.

32. The system of claim 31, wherein the identification data includes bar code data.

33. The system of claim 24, wherein the implantable medical device is a stent.

34. A method, comprising:
   applying a coating composition to a stent;
   using a computer system to determine a characteristic of the coating composition; and
   receiving feedback data from the computer system providing the determined characteristic of the coating composition, the feedback data being used to adjust a parameter when applying a future coating composition, if so determined.

35. The method of claim 34, wherein the application of the coating composition comprises spraying a polymer dissolved in a solvent and optionally a therapeutic substance added thereto to the stent.

36. The method of claim 34, wherein prior to using the computer system to determine the characteristic, the method additionally comprises allowing the coating composition to solidify to form a coating layer.

37. The method of claim 36, wherein the characteristic of the coating composition is the weight or thickness of the coating layer.

38. The method of claim 36, wherein the characteristic of the coating composition is the chemical constituents of the coating layer.

39. The method of claim 34, wherein the characteristic of the coating composition is the components of the coating composition.

40. The method of claim 34, wherein the stent includes a means for allowing the computer system to identify the stent.

41. The method of claim 34, wherein during the application of the coating composition the stent is supported on a mandrel.

42. The method of claim 41, wherein the mandrel includes a means for allowing the computer system to identify the stent.

43. The method of claim 41, wherein the mandrel includes a bar code for allowing the computer system to identify the stent.

44. The method of claim 41, wherein the mandrel is adapted to connect to a motor for rotating the stent about a longitudinal axis of the stent during the application of the coating composition.

45. The method of claim 34, additionally comprising using the computer system to determine whether the determined characteristic is within a scope of a pre-selected characteristic.

46. The method of claim 45, additionally comprising, if the determined characteristic falls outside of the scope of the pre-selected characteristic, adjusting the conditions of the application of the coating composition.

47. The method of claim 46, wherein the adjustment of the conditions is conducted by the computer system.

48. The method of claim 45, additionally comprising, if the determined characteristic falls outside of the scope of the pre-selected characteristic, adjusting the constituents of the coating composition.

49. The method of claim 48, wherein the adjustment is conducted by the computer system.

50. The method of claim 48, wherein the adjustment comprises adjusting the ratio of the ingredients of the coating composition, wherein the ingredients comprise a polymer, a solvent and optionally a drug.

51. The method of claim 48, wherein the adjustment comprises adjusting the ratio of a drug to a polymer of the coating composition.

52. The method of claim 48, wherein the characteristic is a comparison between a measured characteristic and a pre-selected characteristic.

53. The method of claim 52, wherein the characteristic is selected from a group consisting of coating layer thickness, coating layer weight, and the chemical components of a coating layer disposed on the stent.

* * * * *